(12) United States Patent
Hewitson et al.

(10) Patent No.: US 9,274,247 B1
(45) Date of Patent: Mar. 1, 2016

(54) HIGH RESOLUTION DENSITY MEASUREMENT PROFILER USING SILICON PHOTOMULTIPLIER SENSORS

(71) Applicants: John A. Hewitson, Valencia, CA (US); George C. Henry, Westlake Village, CA (US)

(72) Inventors: John A. Hewitson, Valencia, CA (US); George C. Henry, Westlake Village, CA (US)

(73) Assignee: Ronan Engineering Company, Valencia, CA (US)

( * ) Notice: Subject to any disclaimer, the term of this patent is extended or adjusted under 35 U.S.C. 154(b) by 0 days.

(21) Appl. No.: 14/289,580

(22) Filed: May 28, 2014

(51) Int. Cl.
*G01V 5/12* (2006.01)
*G01N 23/12* (2006.01)
*G01N 23/10* (2006.01)
*G01T 1/24* (2006.01)
*G01N 23/08* (2006.01)

(52) U.S. Cl.
CPC ........ *G01V 5/12* (2013.01); *G01N 23/08* (2013.01); *G01N 23/10* (2013.01); *G01N 23/125* (2013.01); *G01T 1/248* (2013.01)

(58) Field of Classification Search
None
See application file for complete search history.

(56) References Cited

U.S. PATENT DOCUMENTS

| | | | | |
|---|---|---|---|---|
| 6,633,625 | B2* | 10/2003 | Jackson | B01D 17/00 250/357.1 |
| 7,164,143 | B2* | 1/2007 | Wainer | 250/497.1 |
| 8,171,785 | B2* | 5/2012 | Aasheim | G01F 23/0076 73/290 R |
| 2003/0122082 | A1* | 7/2003 | Frederick et al. | 250/361 R |
| 2005/0250860 | A1* | 11/2005 | Appleford et al. | 516/135 |
| 2006/0124832 | A1* | 6/2006 | Harmon | G01T 1/24 250/214 R |
| 2006/0192128 | A1* | 8/2006 | Benlloch Bavciera et al. | 250/369 |
| 2006/0293580 | A1* | 12/2006 | Ladebeck | G01R 33/422 600/407 |
| 2008/0284428 | A1* | 11/2008 | Fiedler et al. | 324/307 |
| 2009/0309032 | A1* | 12/2009 | Ramsden | G01T 1/1644 250/370.1 |
| 2012/0312994 | A1* | 12/2012 | Nikitin et al. | 250/362 |
| 2013/0099100 | A1* | 4/2013 | Pavlov | 250/208.2 |
| 2014/0231664 | A1* | 8/2014 | Howe | G01T 7/00 250/395 |

* cited by examiner

*Primary Examiner* — Thomas R Artman
(74) *Attorney, Agent, or Firm* — Thomas I. Rozsa

(57) ABSTRACT

A system to completely measure multiple densities in varying levels in tanks or vessels. The present invention provides a multiplicity of aligned sources and separate aligned detectors, the combination aligned sources and separate detectors are positioned horizontally relative to each other at varying vertical tank levels, each combination separate source and aligned detector at each measuring level in the tank provide continuous density data at each level. The sources and separate detectors are placed in a vertically aligned array in the separation tank near the weir, with each individual source and separate detector aligned with a given level.

17 Claims, 8 Drawing Sheets

5X6.5 TUBE SLIDE-IN SOURCES & DETECTORS LAYOUT

5X6.5 TUBE SLIDE-IN SOURCES & DETECTORS LAYOUT

SLIDE-IN SOURCE UNITS — VIEW A-A ON FIG. 1

SLIDE-IN DETECTOR UNITS — VIEW B-B ON FIG. 1

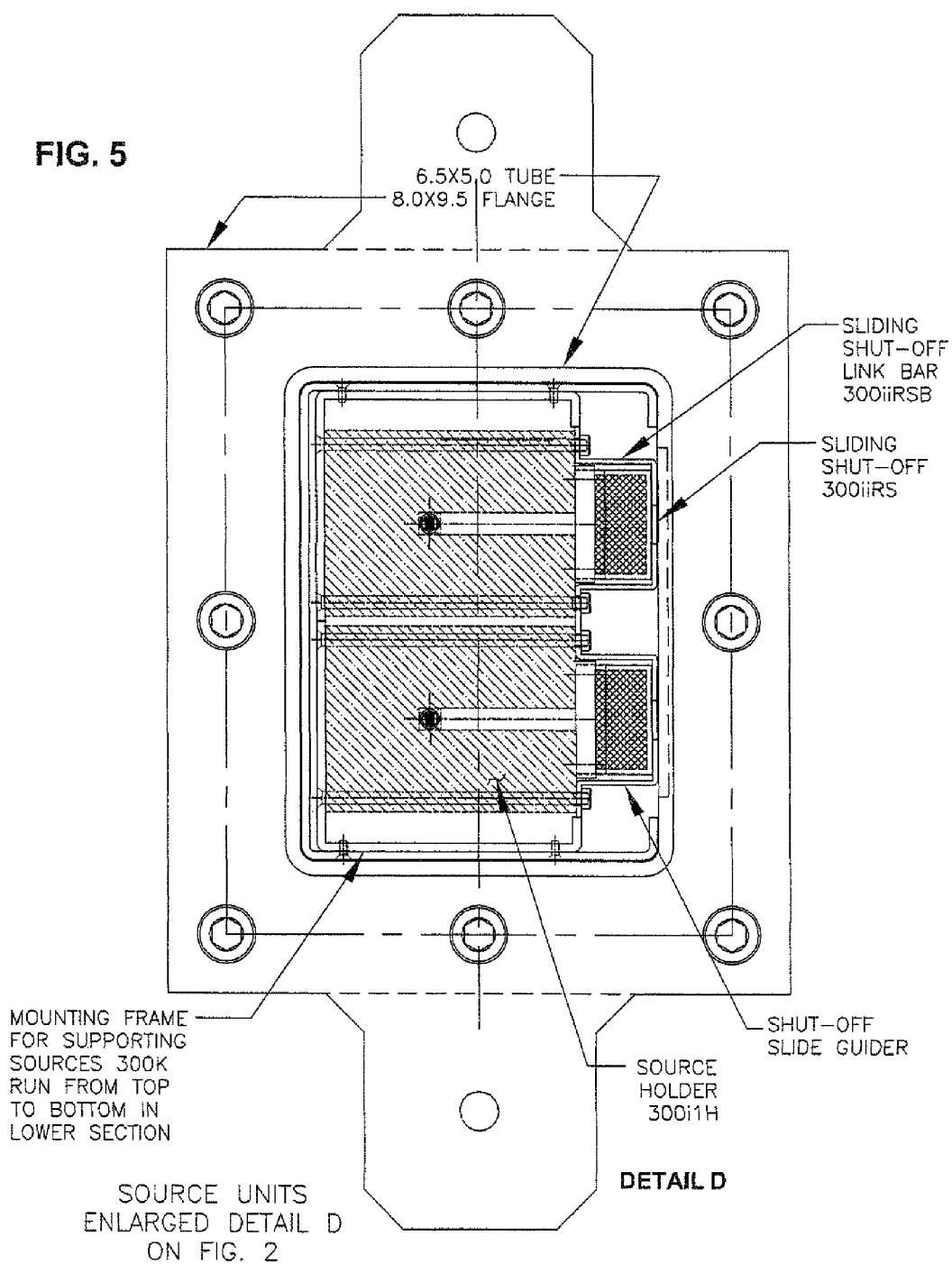

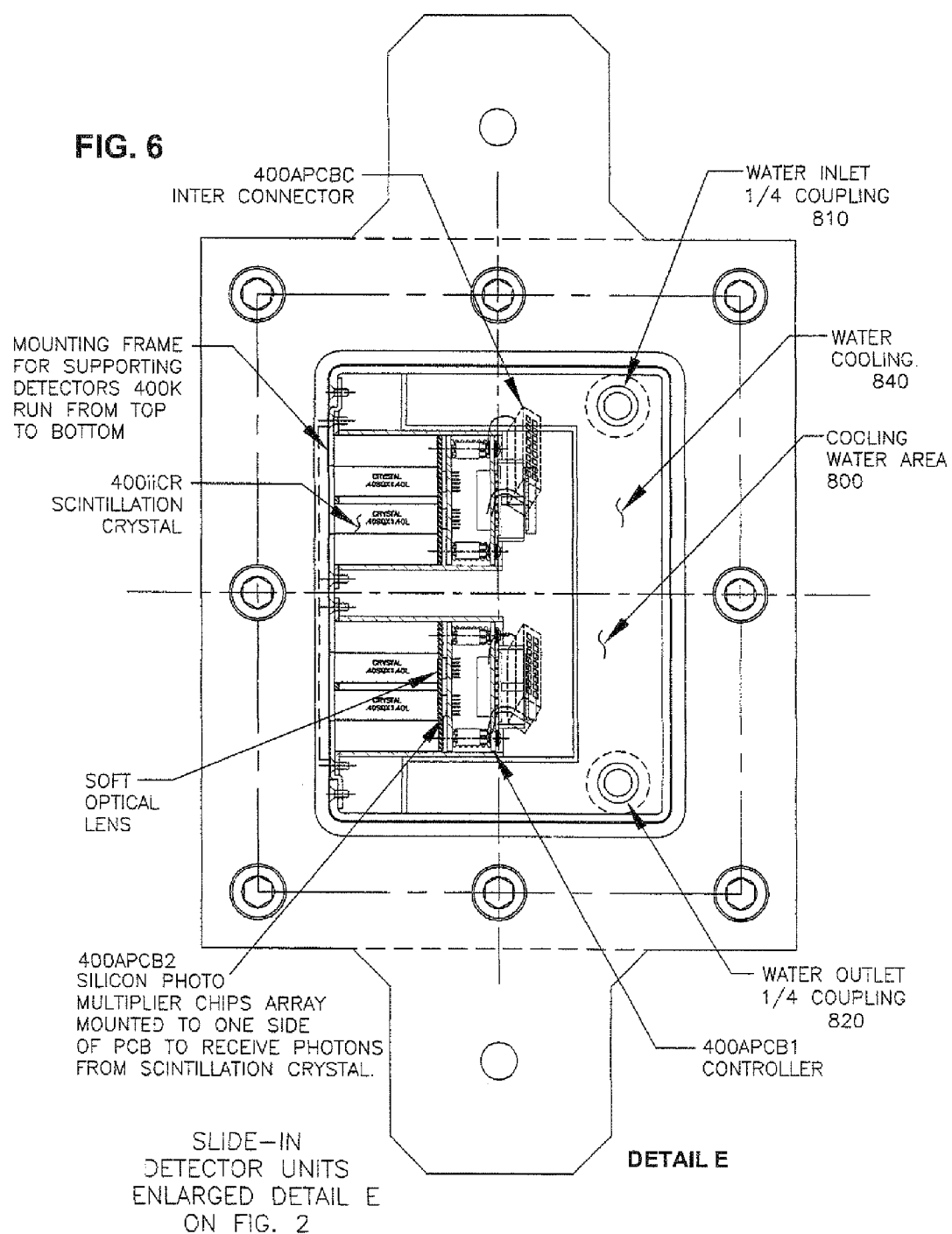

GAMMA SOURCES 300A
PERSPECTIVE VIEW**

RADIATION PROOF SOURCE
HOLDER PERSPECTIVE VIEW**

SOURCES & SHUT-OFF FEATURE SHOWN IN OPEN POSITION

DETECTOR MODULE 400A
PERSPECTIVE VIEW**

DETECTOR MODULE ASSEMBLY
EXPLODED VIEW**

DETECTORS FEATURE SHOWN IN ARRAY

HIGH RESOLUTION DENSITY MEASUREMENT PROFILER USING SILICON PHOTOMULTIPLIER SENSORS

BACKGROUND OF THE INVENTION

1. Field of the Invention

The present invention relates to the field of nuclear measurement of densities, levels and profiles of liquids such as oil and water which have been extracted from the ground either through land drilling or offshore drilling.

2. Description of the Prior Art

In general, conventional methods to determine the percentage of drill results which is oil is known. The prior art sensors are placed in a single longitudinal array, so if a sensor malfunctions, the entire sensor array must be removed from the measuring tank and the defective sensor replaced. This results in downtime as the system must be shut down to replace the malfunctioning sensor in the sensor array. The tank must also be emptied to repair the malfunctioning sensor.

In a profiler system, multiple source and collector systems are placed in a vertical array so material is examined at specified heights within the liquid.

Photomultiplier tubes have many undesirable characteristics when used in systems designed to measure potentially explosive components of oil. These include:
a. High voltage potentials in the range of 1 KV are required to bias the PMT. These can spark explosions and must be carefully contained so they do not penetrate the fluid they are measuring.
b. Generate considerable heat which requires an external cooling system. Usually, cooled water is pumped through water jackets surrounding the part.
c. Electrical performance is degraded over time and temperature, again requiring external cooling equipment and frequent re-calibration.
d. PMT's are sensitive to stray magnetic fields often needing magnetic shielding to avoid spurious measurement errors.
e. Being constructed from delicate mechanical components and housed in glass packaging makes PMTs very fragile.
f. Performance from unit to unit is highly variable requiring careful and time consuming "in system" calibration. This usually requires the system to be shut down resulting in significant production dead time.

There is a significant need for an improvement in the prior art systems.

SUMMARY OF THE INVENTION

The present invention is a system to completely measure multiple densities in varying levels in tanks or vessels. The present invention provides a multiplicity of aligned sources and separate aligned detectors, the combination aligned sources and separate detectors are positioned horizontally relative to each other at varying vertical tank levels, each combination separate source and aligned detector at each measuring level in the tank provide continuous density data at each level.

The flow of oil and other materials is pumped out of the ground, either through on-land drilling or offshore drilling and then the oil and remaining materials are caused to flow into a separation tank through an inlet. The oil and other materials are separated by gravity, heating and time. The heaviest material which usually is sand falls to the lowest level. The second heaviest material which is water falls to the next higher level. The third heaviest material which is emulsion flows to the next higher level. The lightest material which is oil floats on the top level. The oil is caused to flow over a weir which is a filter. However, until a measurement from the present invention is made, the location of each of these materials is not known.

The sources and separate detectors are placed in a vertically aligned array in the separation tank near the weir, with each individual source and separate detector aligned with a given level.

Nuclear measurement of densities, levels, and profiles of liquids is based on gamma rays generated by a nuclear isotope being transmitted in a narrow beam through the measured material. The number of gamma particles penetrating a specific material will vary with its density. The several hydrocarbon components and sand all have different densities which may be determined by the system. The first portion of the detector is a scintillation crystal which captures gamma particles making it through the material and converts impinging gamma particles to visible photons. A two-stage collector is positioned downstream from the scintillation crystal in the detector. The first collector stage is a silicon photomultiplier chips array mounted to one side of a printed circuit board to receive photons from the scintillation crystal. The silicon photomultiplier array produces an electrical output signal each time it detects a visible photon emitted from the crystal. A second collector stage controller board which is interconnected with the silicon photomultiplier array board consists of a pre-amplifier, a signal detector and a counter. Together these circuits receive, amplify and shape the electrical signals received from the silicon photomultiplier array into a stream of voltage pulses which are then counted over measured time intervals. Periodically the electronic count data is transmitted over a ribbon cable to an analysis computer.

The final electric output is processed in a computer to determine the density of the liquid.

The present invention replaces the conventional Vacuum Photomultiplier Tube (PMT) and Geiger-Muller Tube (GMT) with an integrated circuit device called a Silicon Photomultiplier (SiPM) that closely resembles their operation. It collects photons generated in crystals by gamma particles enabling single photon counting so output signal processing can be done the same way as with the Vacuum PMT and GMT. Several characteristics of the PMT and GMT are improved:
a. The SiPM has maximum operating voltage of 30 Vdc compared to 500 to 1,000 Vdc for vacuum PMTs and GMT tubes. This reduces cost and space of support electronics and simplified safety feature design when used in explosive environments.
b. Since the silicon device is very small and generates very little heat, it can be cooled locally with a small electronic cooler.
c. As with most semiconductor devices, it has no wear out mechanisms and can be operated indefinitely with no performance degradation.
d. The silicon photomultiplier chips have a 5 MHZ bandwidth which raises the maximum count rate to 5,000,000 counts per second. This is 10 to 20 times conventional photomultiplier tubes ("PMT") and Geiger Muller ("GMT") tubes. Alternatively stated, bandwidth of the SiPM is an order of magnitude greater than PMT or GMT tubes allowing ten times faster and higher measurements to be made. Precision measurements can be made 10-20 times faster to provide real time profiles in turbulent fluids. Alternatively stated, higher precision measurements are made in equal times.

e. Device size is reduced by more than an order of magnitude enabling much smaller detector packaging.

r. The SiPM is inherently more robust and is insensitive to magnetic fields and mechanical vibrations.

g. Device models may be selected to optimize a number of system needs such as measurement accuracy, resolution and range.

h. The SiPM has consistently tight performance specs from unit to unit because of the wafer scale integrated circuit manufacturing process.

i. SiPM cost is potentially lower than the vacuum PMT and GMTs due to modern integrated circuit manufacturing methods.

j. The SiPM can easily be retrofitted into systems that presently use a vacuum PMT.

It is an object of the present invention to provide a system to completely measure multiple densities in varying levels in tanks or vessels. The present invention provides an individual source and separate detector at each measuring level in the tank, each source and separate detector providing continuous density data at each level.

It is an object of the present invention to provide separate source and detector arrays that are inserted into separate protective sleeves which can be permanently installed in the tank having different process fluid flow distances to facilitate optimal detection of the particular fluids planned to be processed.

It is an object of the present invention to provide a system where the flow through each section of each source/detector pair can be equipped with tubing and nozzles to clean the source and detector surfaces during normal operation to maintain the best possible reading of the profiler.

It is a further object of the present invention to provide a system where the flow of oil and other materials is pumped out of the ground, either through on-land drilling or offshore drilling and then the oil and remaining materials are caused to flow into a gravity separation tank through an inlet. The heaviest material which usually is sand falls to the lowest level. The second heaviest material which is water falls to the next higher level. The third heaviest material which is emulsion flows to the next higher level. The lightest material which is oil floats on the top level. After the oil has separated from the other materials it is caused to flow over a weir which is a filter. However, a measurement through the present invention is necessary to accurately determine the type and location of each material before allowing oil to flow over the weir.

In summary, the key features of the present invention linear profiler design are as follows:

a. Application of the silicon photomultiplier chips in the profiler design.

b. Removable design of each source array and detector array from their respective sleeves in the separation tank.

c. Cooling of the detector array to improve performance of each silicon photomultiplier chips and its control circuitry.

d. Source array provided with on-off feature to inhibit radiation leakage when withdrawing or transporting the source array.

e. Source array provided with an automated on/off feature which is under computer control to enhance system calibration accuracy.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 shows the insertion of two 6.5×5" tubes into the separation tank which are described as the dip tube-1 and dip tube-2 (Rectangular tubes-1 and -2) for the nuclear source probes and electronic detection probes;

FIG. 5 is a top plan view of the source holders described in FIG. 3;

FIG. 6 is a top plan view of the detector holders described in FIG. 4;

DETAILED DESCRIPTION OF SELECTED EMBODIMENTS TO ILLUSTRATE OPERATIVE EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

When oil is pumped out of the ground, wether through on-land or offshore drilling, the oil gushes out of the ground accompanied by many other materials. The gushing oil is fed into a separation tank so that its contents can be analyzed.

Figure 1:
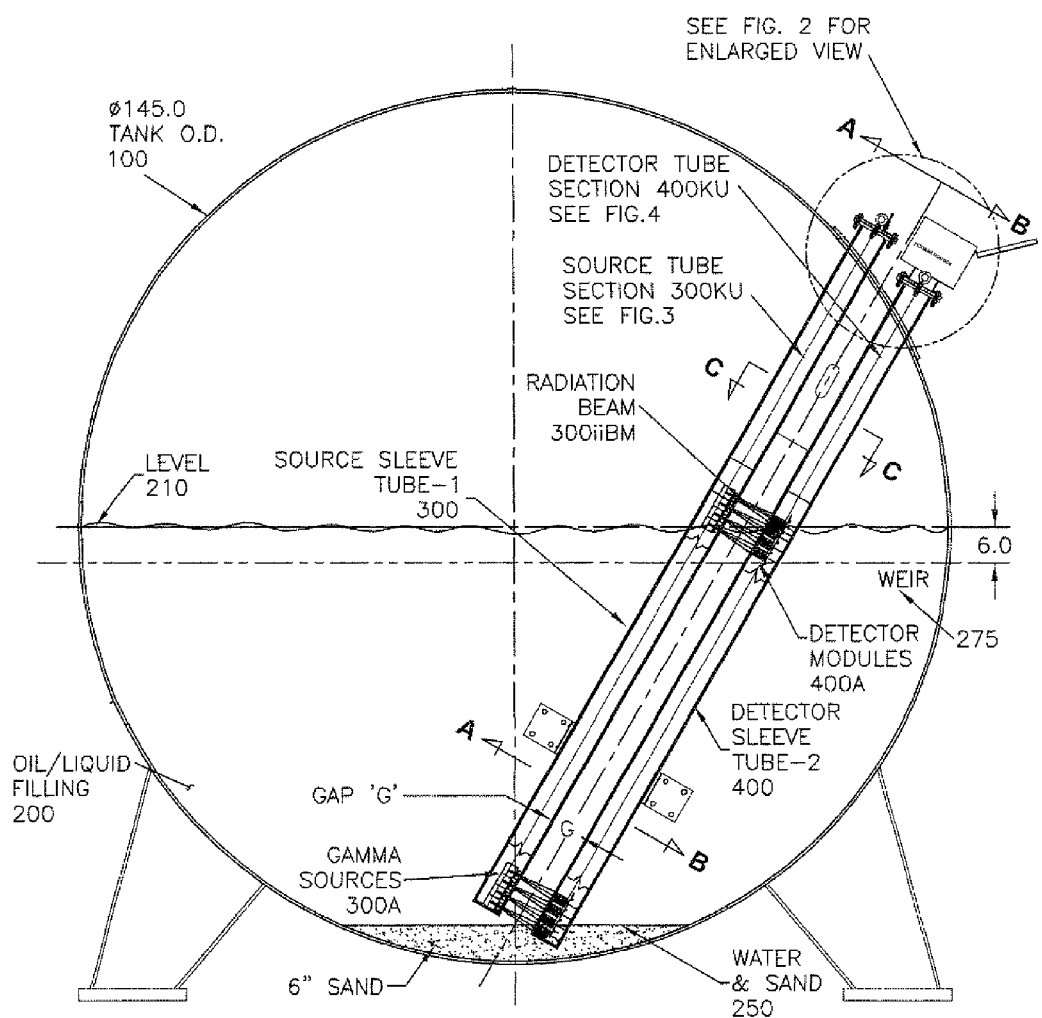
FIG. 1 is a cross-sectional view of a separation tank, illustrating the profiler instrument with the separate source and detector arrays placed in separate protective sleeves, the vertical row of sources is horizontally aligned with the vertical row of detectors, with each respective source separated from its aligned detector by a gap, determined by the placement of sleeves in the tank, in addition.
Figure 2:
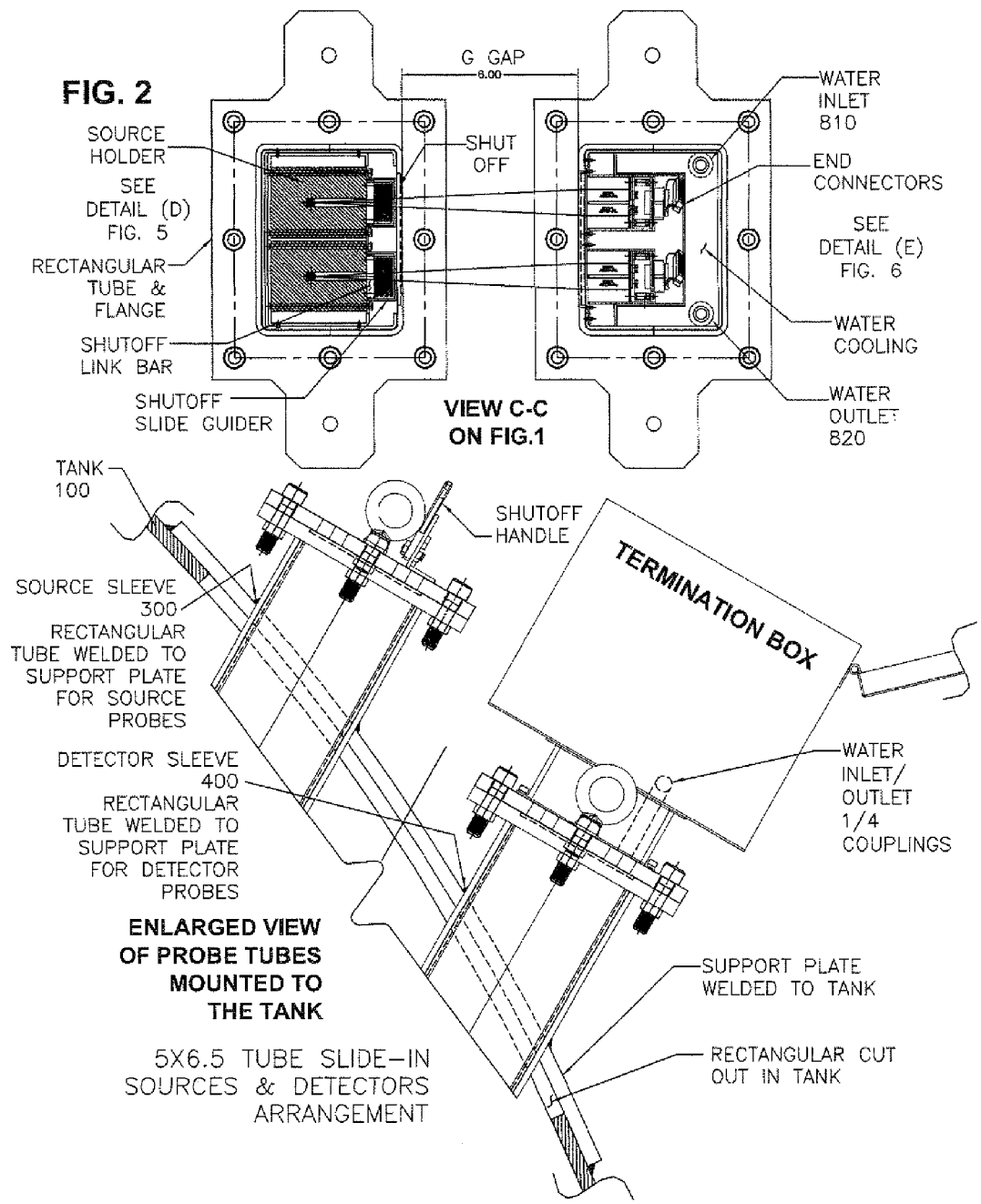
FIG. 2 is a top plan and partial side view taken from C-C of FIG. 1, illustrating the source and detector arrays, showing two adjacent vertical rows side by side and illustrating the sleeves mounted to and into the separation tank.

Referring to FIG. 1, there is illustrated a cross-sectional view of the separation tank 100 which can have an outer diameter of 145 inches with oil and its contents designated as liquid 200 filling the separation tank 100 to a given level 210. Sand and water 250 is usually the heaviest and falls to the bottom of the separation tank 100. The other materials are at different liquid levels. Referring to FIGS. 1 and 2, the rectangular tubes for the source holders and detector holders are welded to a support plate at the top of the separation tank, with a separate support plate and holder for the first vertical sleeve 300 and a second support plate and holder for the second vertical sleeve 400. The first vertical sleeve 300 is welded so that it is adjacent the top of the separation tank or a sidewall of the separation tank and adjacent the bottom of the separation tank and placed in a lower sand level which is adjacent the bottom of the separation tank 100 and thereafter welded in place at the circumferential wall of the separation tank. Similarly, a second sleeve 400 runs from a distance above the top of the separation tank and is positioned to rest adjacent the bottom of the separation tank 100 or at least into the sand level adjacent the bottom of the separation tank. The second sleeve 400 is also welded to the top of the separation tank as described. The purpose of the sleeve which is usually made of a very thin sheet of metal is to separate the dip tube-1 retaining the gamma sources and the dip tube-2 retaining the detectors from the fluid 200 in the tank so that there is a clear separation between the sources and the detectors so that they will not become dirty from the fluid in the tank. This is a significant improvement of the present invention which, among other features, distinguishes it over known prior art where the sources and detectors are mixed with the fluid and become dirty. The very thin sheet of metal such as steel which is less than 1/16 inch will not materially affect the radiation beams' transmittal through the fluid in the gap between each source of gamma radiation and its aligned detector module. By way of example, each dip tube-1 and dip tube-2 can have cross-section sides of 6.5" by 5" while the sleeve into which it is inserted will have a cross-section slightly larger so there is a tight fit. The present invention profiler is comprised of a vertical array of sources such as gamma sources 300A and a vertical array of detector modules 400A. The vertical array of sources 300A are retained in a first dip tube-1 300K (see FIGS. 1 and 3) and the vertical array of detector modules 400A are aligned in a second dip pipe 400K (See FIGS. 1 and 3). Each respective one of the vertical array of sources 300A is horizontally aligned with a respective one of the vertical array of detector modules 400A and the entire array of gamma sources 300A are separated from the entire array of detector modules 400A by a gap "G" (See FIG. 1). The actual separation is from the first sleeve into which the first dip tube-1 300K is inserted and the second sleeve into which a second dip tube-2 400K is inserted. The array of sources 300A can comprise any multiplicity of individual gamma sources and the array of detector modules 400A can comprise any multiplicity of detector modules.

Figure 3:
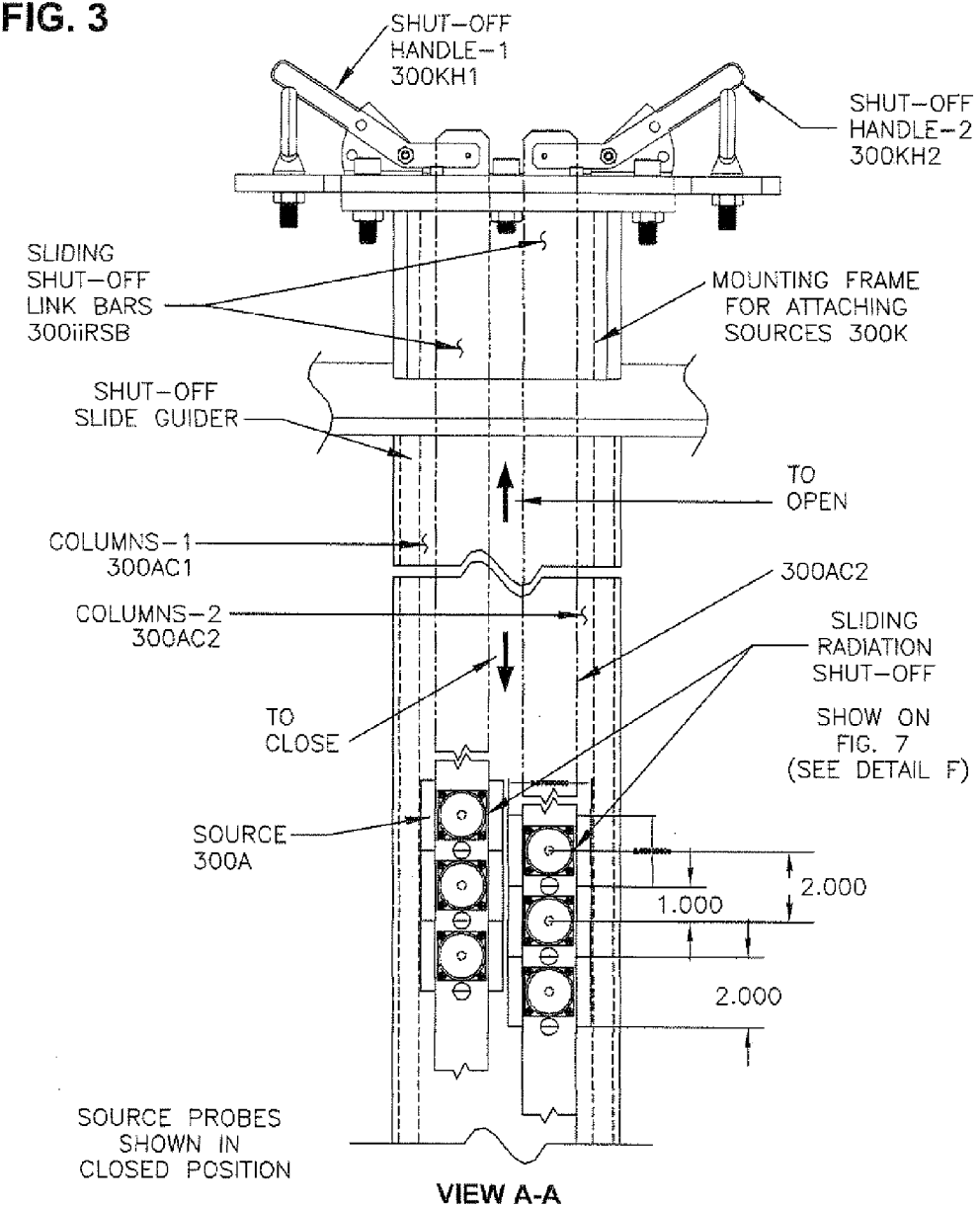
FIG. 3 is a partial cross-sectional view of the source holder assembly taken along line A-A of FIG. 1, the present invention linear profiler illustrating two separate source columns 300AC1 and 300AC2; with each source column mounted to a separate shut-off slide connected to a separate shut-off handle 300KH1 and 300KH2 to permit each source column to be independently shut off.
Figure 7A:
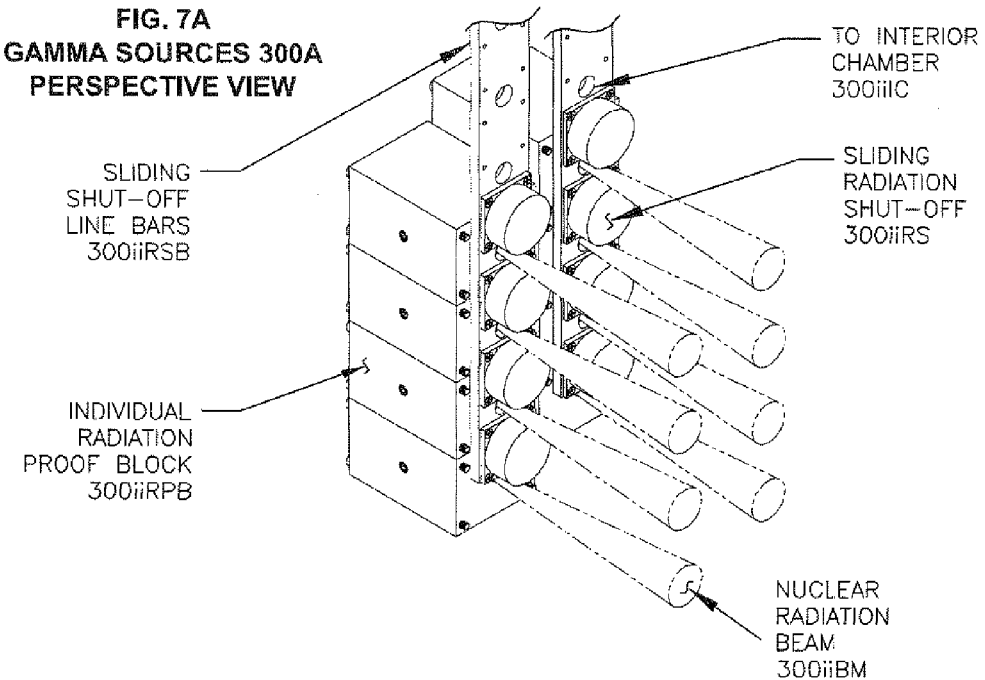
FIG. 7A is a perspective view of individual source holders including sliding shut-off link bars, sliding radiation shut-off, and collimation opening for radiation, and nuclear source insert.

As illustrated in FIGS. 1, 2 and 3, the first dip pipe 300K retains the array of sources 300A (described herein as gamma sources but other sources are within the spirit and scope of the present invention in a vertically offset aligned columns 300AC1 and 300AC2. The first dip tube-1 300K comprises an elongated upper pipe section 300KU and an elongated lower pipe section 300KL which retains the array of sources 300A. FIG. 2 is an enlarged view of the source and detector array which will be further described in detail later in the application. As illustrated on FIG. 3, the first dip tube-1 300K (see FIG. 1) has a first shutoff handle 300KH1 and a second shutoff handle 300KH2 at the top of each respective column 300AC1 and 300AC2. Each shutoff handle is open. Therefore, the shutoff handles are located far away from the source array 300A. FIG. 5 and FIG. 7A illustrate a top plan view of this assembly with the sliding shutoff link bar 300iiRSB, sliding shutoff 300iiRS, the source holder 300i1H and the source holder back support.

Figure 7B:
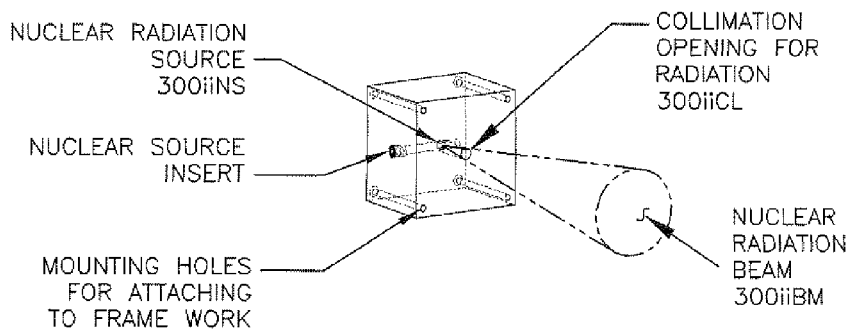
FIG. 7B is a perspective view of an individual radiation proof block showing how the nuclear radiation source is inserted relative to the radiation beam collimation opening.

Referring to FIGS. 7A and 7B, there is illustrated an individual one of the source 300ii in the source array 300A. Each individual source 300ii (see FIG. 1) includes a source block 300iiRPB which is made from radiation absorbing metal enclosing an interior chamber 300iiIC within which is retained a nuclear source of radiation 300iiNS such as gamma radiation and a collimator 300iiCL for transmitting a nuclear radiation beam 300iiBM (see FIG. 1) through the first sleeve across the gap "G" (see FIG. 1) through the second sleeve to an aligned detector in the detector array 400A. Sliding radiation shutoff line bars 300iiRS affixed to sliding shut-off line bars 300iiRSB is shown in the opened condition, as in FIG. 7A. When slid down in the closed condition, a radiation shut-off 300iiRS prevents the radiation beam 300iiBM from passing through the collimator 300iiCL.

Figure 4:
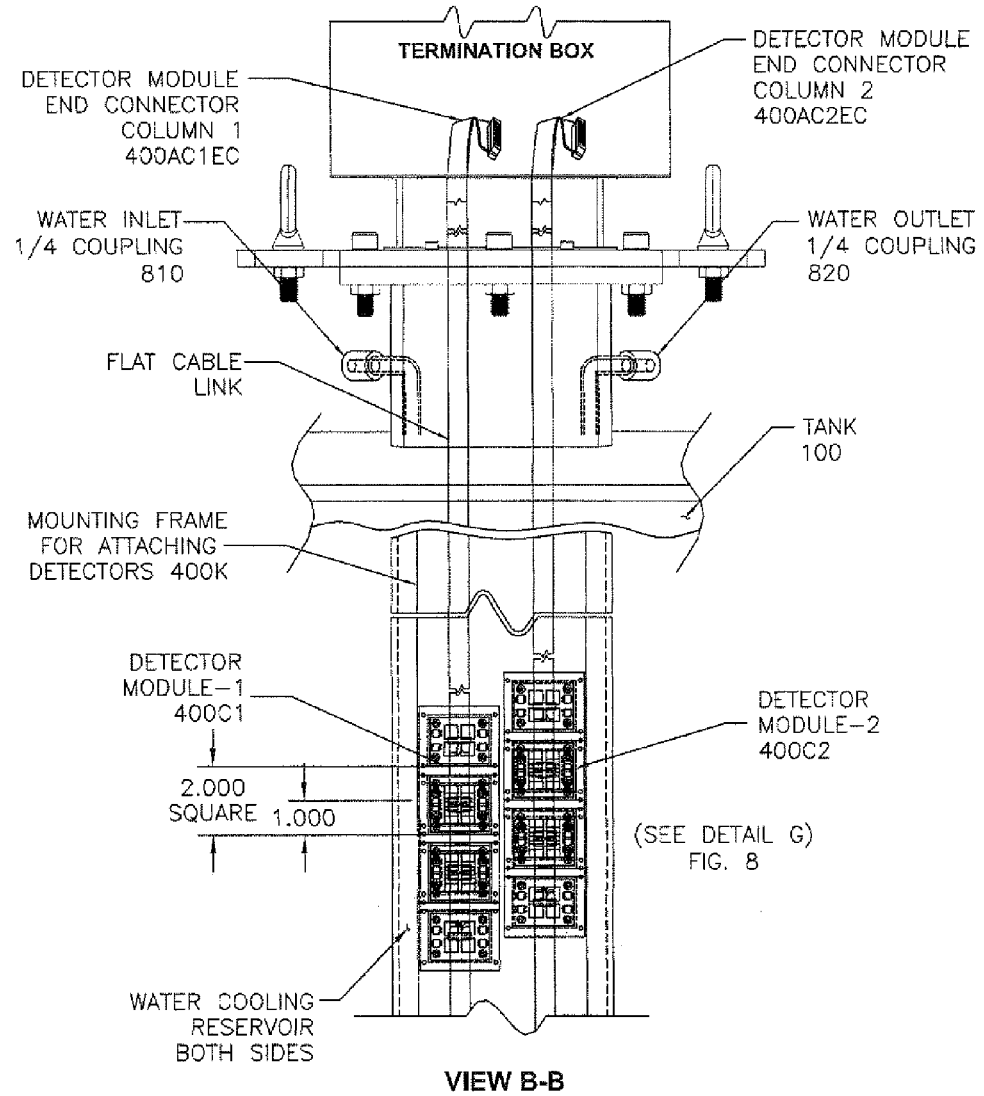
FIG. 4 is a partial cross-sectional view of a detector holder assembly taken along line B-B of FIG. 1, of the present invention profiler illustrating a detector including two separate detector columns mounted on two vertical flat bar rods to align with its source pair when mounted in the tank.

As illustrated in FIGS. 1 and 4, the second dip tube-2 retains an array of detector modules 400A in vertically offset aligned columns 400C1 and 400C2. The second dip tube-2 400KL (see FIG. 1). As illustrated in FIG. 4, each column 400C1 and 400C2 has a respective end connector 400AC1EC and 400AC2EC by which a respective column 400C1 and 400C2 can be removed. FIG. 6 illustrates a top plan view of this assembly further illustrated with detector modules 400A with a detector SiPM and controller circuit board 400APCB1 and 400APCB1 (see FIG. 6). Referring to FIG. 2, the first dip tube-1 300K is inserted into the separation tank 100 through an opening in the first sleeve. The second dip tube-2 400K is inserted into the separation tank 100 through an opening in the second sleeve.

Figure 8A:
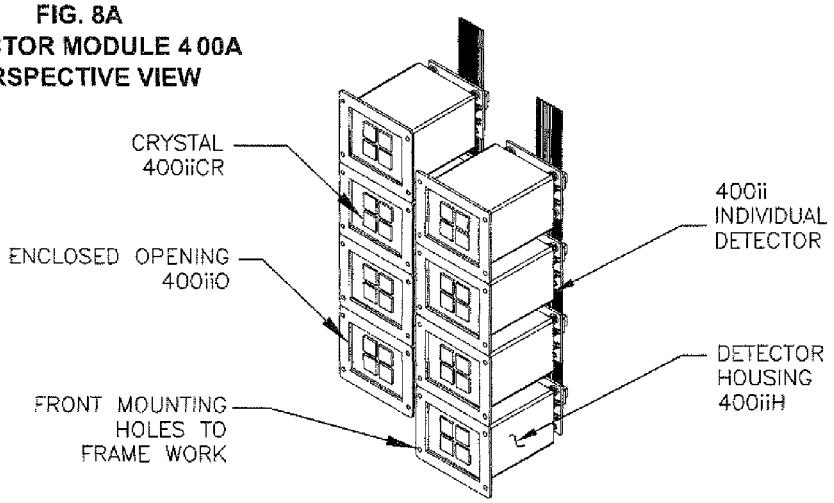
FIG. 8A is a perspective view of individual detector holders, crystal and ribbon cable which is attached to each detector unit finally terminating in a termination enclosure.
Figure 8B:
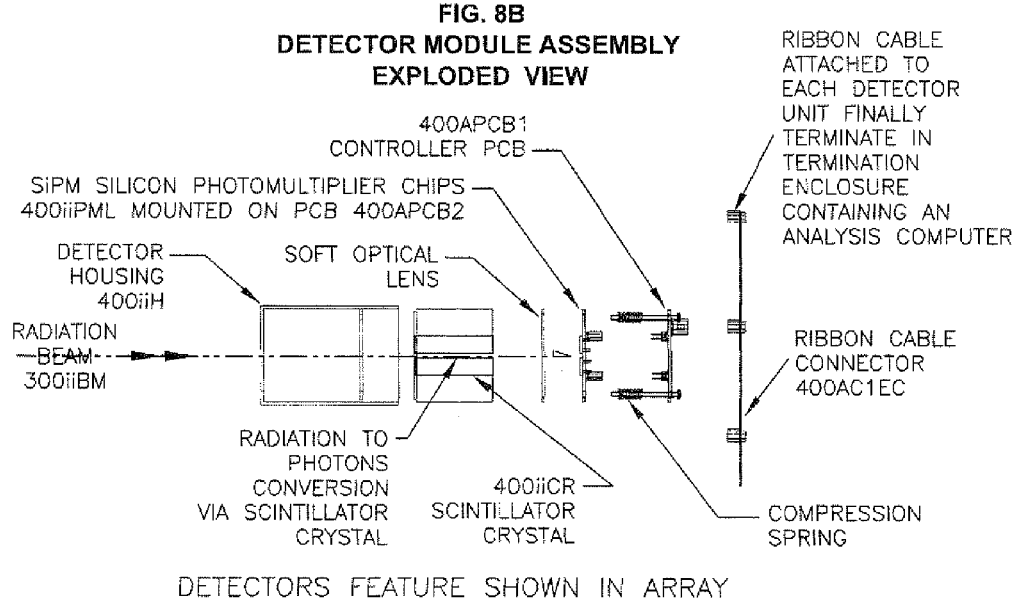
FIG. 8B shows and exploded assembly sequence of the separate detector components.

Referring to FIGS. 8A and 8B, there is illustrated an individual detector module 400ii which is enclosed in housing 400iiH with the walls and an opening 400iiO to receive a scintillation crystal housing 400iiCR. Referring to FIG. 8B, the radiation beam 300iiBM from nuclear radiation source enters the detector housing 400iiH. The detector housing 400iiH retains a scintillation crystal 400iiCR which captures particles from the radiation beam, which particles were able to pass through the liquid 200 in the gap G. The scintillation crystal converts some of the gamma photons to visible photons which are directed through a soft optical lens towards a two stage detector. The first stage mounted on PCB 400APCB2 contains an array of SiPM chips and analog amplifiers. The SiPM chips convert visible photons into electrical analog signals which are amplified and sent through inter board connectors to a second stage controller PCB 400APCB1. The controller measures and counts the analog signals and digitizes and transmits results to a digital bus implemented with ribbon cables and connectors 400ACHEC. The ribbon cables connect all the detectors in each respective column to an analysis computer ANCMCT which analyzes the density and separates the elements in the liquid at the specific level between the specific radiation source and the detector module into percentages of sand, water, emulsion and oil. The analysis computer calculates the density of the oil/liquid 200 in the tank 100 based on the number of photons which passed through the oil/liquid 200 in the gap "G" between the source array 300A and the detector array 400A in tank 100. The analysis computer ANCOMPT uses known computer programs to compute the amount and percentage of sand, water emulsion and oil in the liquid 200 at each level monitored by a radiation source and detector module. FIG. 6 also illustrates the silicon photomultiplier chips array mounted onto one side of the printed circuit board PCB 400APCB2 which receives photons from the scintillation crystal The PCB controller 400APCB1 and sensor array printed circuit board 400APCB2 with a respective offset source 300A with a nuclear source 300iiNS is aligned with a respective offset detector module 400A with a scintillation crystal 400iiCR.

The path of the radiation beam 300iiBM from the nuclear source capsule 300iiNS to the scintillation crystal 400iiCR is illustrated in FIG. 1, The source 300A and detector 400A are separated by a gap "G" which enable fluid 200 flow through the gap.

The following components are also illustrated in FIG. 6: a cooling area 800 having a water inlet coupling 810 through which cooling water 840 flows and a water outlet coupling 820 through which cooling water exits. The cooling water 840 is held in a large tank reservoir (not illustrated) and cooling water 840 is forced from the reservoir through the water inlet coupling 810, through the cooling pipe 800, and through the exit water outlet coupling 820 and is re-circulated in this way to cool the following components with the cooling water 840: a scintillation crystal 400iiCR in a detector 400ii. It is these components which are cooled by the cooling water 840 flowing through the cooling pipe 800 which surrounds and envelops these components.

The present invention is a three-phase petroleum profiler having the following key innovations:

(a) The present invention is a measurement and analysis system that measures density to identify the types and vertical boundaries of sand, water, emulsion and oil in petroleum settling tanks;

(b) The present invention is used in upstream separation tanks 100 where its enhanced accuracy, resolution, and millisecond response to dynamic level changes enables the highest production rates;

(c) Settling tanks rely on gravity, time, and heat to separate effluent components. Since each material has a different density, gravity will over time cause the heaviest to sink to the bottom and the lightest to rise to the top of the tank. Heating the effluent accelerates this process improving production throughput;

(d) Gases rise to the top of the tank and are pumped out to the next process step. The maximum level of liquids and solids is limited by a weir 275 (See FIG. 1) at the output end of the tank. Oil, being the lightest of these, rises to the top and overflows the weir 275 into a collection area. Water and sand 250 settle to the bottom and after the analysis set forth above are removed through a control valve at the bottom of the tank 100;

(e) Processing produces foam on top of the oil layer. Foam level is controlled by adding chemicals to prevent it passing over the weir 275, as foam in the oil adds unwanted water. The foam level must be accurately measured and reported in real time so chemical usage and process throughput can be optimized;

(f) An emulsion layer of oil and water exists between the oil and water layers. The system must measure and report the extreme boundaries of the emulsion to insure only "in spec oil" is allowed to pass over the weir 275 and that expelled water and sand do not violate regulatory contamination standards;

(g) The present invention system measures many times more material to achieve higher accuracy with far more tolerance to build up compared to conventional technology;

(h) Well fluids 200 enter the tank 100 and are subject to surges and gaps which can cause rapid changes, even waves in fluid levels. Conventional equipment must increase guard bands of "IN-Spec Oil" layers which reduces processing rates. The present invention tracks level changes many times faster than present technology, allowing reaction time for automating tank flows with motorized valves.

The present invention works as follows:

(a) Vertical arrays of gamma sources 300A and detector modules 400A are housed in two dip tubes, dip tube-1 300K and dip tube-2 400K lowered into the tank 100—one each for sources and detectors;

(b) Each source 300ii has an on/off mechanical radiation shield 300iiRSB which serves to block gamma rays 300iiBM when off and collimates them through a collimator 300iiCL in a narrow beam 300iiBM when on. The shields 300iiRS are ganged together and may be switched manually or under the system computer's control allowing more accurate in situ calibrations;

(c) Each source 300ii in the first dip tube-1 300K pairs with a detector 400A in the second dip tube-2 400K. These are horizontally aligned at the same depth in the tank and oriented so the gamma beam 300iiBM between them is perpendicular to process flow. Distance "G" between the sources 300A and detectors 400A is chosen to allow the gamma beam 300iiBM to intercept 10 to 40 cm of process flow depending on nominal characteristics of a well's effluent;

(d) The scintillation crystal 400C1 collects those gamma rays 30iiBM making it through the process and converts them to visible photons. A new state of the art silicon photomultiplier chip senses the individual photons and generates electrical signals that are counted by a local micro controller;

(e) A master controller continuously collects counter values from the detectors, interprets material densities, and communicates the results to the control room.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. An apparatus inserted into and used in conjunction with a separation tank containing liquid pumped out of land from in-land or offshore drilling, and used to analyze the contents and density of the liquid at different levels within the separation tank, the apparatus comprising:

a. an array of nuclear sources, each nuclear source including a source holder, said source holder having radiation proof walls enclosing an interior chamber, wherein at least one of said radiation proof walls including an opening;

b. a nuclear source of gamma radiation located within said interior chamber and configured to emit a nuclear gamma radiation beam through said opening;

c. a collimator aligned with said opening and configured to spread said nuclear gamma radiation beam emitted through said opening;

d. an array of detector modules, each individual detector module enclosed in a housing, said housing having walls and an interior opening, said each individual detector module further including a scintillation crystal configured to convert incident nuclear gamma radiation to visible photons, a silicon photomultiplier chip configured to convert incident photons emitted by said scintillation crystal to electrical signals, an electrical pulse generator configured to receive said electrical signals and generate electrical pulses corresponding to said incident nuclear gamma radiation, and an electrical pulse summing member configured to sum a number of electrical pulses generated by said electrical pulse generator; and e. a liquid analysis member configured to receive said summed electrical pulses from each of said individual detector modules;

f. wherein said array of nuclear sources and said array of detector modules are retained within a liquid in a tank such that each nuclear source is aligned with a corresponding said individual detector module in opposition to each other and separated by a gap, said nuclear gamma radiation beam emitted through said opening and spread by said collimator traverses said gap and impinges upon said scintillation crystal of the corresponding said individual detector module;

g. wherein said liquid analysis member configured to determine a density of said liquid and a percentage of sand, water, emulsion and oil in the separation tank for each nuclear source and corresponding detector module pair based on said received summed pulses from each of said electrical pulse generator.

2. The apparatus in accordance with claim 1, further comprising: each silicon photomultiplier chip has a 5 MHZ bandwidth.

3. The apparatus in accordance with claim 1, further comprising:
a. the array of nuclear sources is retained in a first dip pipe and the array of detector modules is retained in a second dip pipe;
b. at least one opening in a top location of the separation tank through which a first sleeve is inserted and retained in the separation tank and a second sleeve is inserted and retained in the separation tank,
c. the first sleeve having a first opening and the second sleeve having a second opening, the first dip pipe inserted into the first sleeve and then inserted into the separation tank and the second dip pipe inserted into the second sleeve and then inserted into the separation tank; and
d. said gap is located between said first sleeve and said second sleeve.

4. The apparatus in accordance with claim 1, further comprising: the array of nuclear sources is in two adjacent offset columns and the array of detectors is in two adjacent offset columns, with the array of nuclear sources in a first column respectively offset from the array of nuclear sources in a second column.

5. The apparatus in accordance with claim 1, further comprising: each nuclear source of the array of nuclear sources is a nuclear isotope.

6. The apparatus in accordance with claim 1, further comprising: each respective pulse generation member is on a printed circuit board and each respective silicon photomultiplier chip is mounted on the printed circuit board.

7. The apparatus in accordance with claim 1, further comprising a cooling apparatus.

8. An apparatus inserted into and used in conjunction with a separation tank containing liquid pumped out of land from in-land or offshore drilling, and used to analyze the contents and density of the liquid at different levels within the separation tank, the apparatus comprising:
a. an array of nuclear sources, each nuclear source including a source holder, said source holder having radiation proof walls enclosing an interior chamber, wherein at least one of said radiation proof walls including an opening;
b. a nuclear source of radiation located within the interior chamber and configured to emit a nuclear radiation beam through said opening;
c. a collimator aligned with said opening and configured to spread said nuclear radiation beam emitted through said opening; and
d. an array of detector modules, each individual detector module enclosed in a housing, said housing having walls and an interior opening, each said individual detector module further including a scintillation crystal configured to convert incident nuclear radiation to visible photons, a silicon photomultiplier chip configured to convert incident photons emitted by said scintillation crystal to electrical signals, an electrical pulse generator configured to receive said electrical signals and generate electrical pulses corresponding to said incident nuclear radiation, and an electrical pulse summing member configured to sum a number of electrical pulses generated by said electrical pulse generator; and
e. a liquid analysis member configured to receive said summed electrical pulses from each of said individual detectors;
f. wherein said array of nuclear sources and said array of detector modules are retained within a liquid in a tank such that each nuclear source is aligned with a corresponding said individual detector module in opposition to each other and separated by a gap, said nuclear radiation beam emitted through said opening and spread by said collimator traverses said gap and impinges upon said scintillation crystal of the corresponding said individual detector module;
g. wherein said liquid analysis member configured to determine a density of said liquid and a percentage of sand, water, emulsion and oil in the separation tank for each nuclear source and corresponding detector module pair based on said received summed pulses from each of said electrical pulse generator.

9. The apparatus in accordance with claim 8, further comprising: each silicon photomultiplier chip has a 5 MHZ bandwidth.

10. The apparatus in accordance with claim 8, further comprising:
a. the array of nuclear sources is retained in a first dip pipe and the array of detector modules is retained in a second dip pipe;
b. at least one opening in a top location of the separation tank through which a first sleeve is inserted and retained in the separation tank and a second sleeve is inserted and retained in the separation tank,
c. the first sleeve having a first opening and the second sleeve having a second opening, the first dip pipe inserted into the first sleeve and then inserted into the separation tank and the second dip pipe inserted into the second sleeve and then inserted into the separation tank; and
d. said gap is located between said first sleeve and said second sleeve.

11. The apparatus in accordance with claim 8, further comprising: the array of nuclear sources is in two adjacent offset columns and the array of detectors is in two adjacent offset columns, with the array of nuclear sources in a first column respectively offset from the array of nuclear sources in a second column.

12. The apparatus in accordance with claim 8, further comprising: each nuclear source of the array of nuclear sources is a nuclear isotope.

13. The apparatus in accordance with claim 8, further comprising: each respective pulse generation member is on a printed circuit board and each respective silicon photomultiplier chip is mounted on the printed circuit board.

14. The apparatus in accordance with claim 8, further comprising a cooling apparatus.

15. The apparatus in accordance with claim 8, further comprising: each nuclear source or radiation is a nuclear source of gamma radiation.

16. An apparatus used to analyze the contents and density of a liquid at a level in a tank, the apparatus comprising:
   a. a nuclear source of radiation within the liquid transmitting a beam of nuclear radiation; and
   b. at least one detector module located in line with the source of nuclear radiation in order to receive the transmitted beam of nuclear radiation, the detector module separated from the source of radiation by a gap, the detector module including a scintillation crystal configured to convert the received beam of nuclear radiation to visible photons, a silicon photomultiplier chip configured to convert the visible photons emitted by the scintillation crystal to electrical signals, an electrical pulse generation member configured to receive the electrical signals and generate electrical pulses corresponding to the received beam of nuclear radiation, an electrical pulse summing member configured to sum a number of the electrical pulses generated by the electrical pulse generation member, and a liquid density analysis member configured to receive the summed electrical pulses from the electrical pulse summing member and configured to determines the amount and percentages of a composition of materials within the liquid at the level of the nuclear source of radiation and the at least one detector module.

17. The apparatus in accordance with claim 16, further comprising: said silicon photomultiplier chip has a 5 MHZ bandwidth.

* * * * *